United States Patent
Machuca et al.

(10) Patent No.: US 10,545,087 B2
(45) Date of Patent: Jan. 28, 2020

(54) DISPOSABLE LIQUID CHEMICAL SENSOR SYSTEM

(71) Applicant: ENTEGRIS, INC., Billerica, MA (US)

(72) Inventors: Francisco Machuca, Oakland, CA (US); Ronald P. Chiarello, Lafayette, CA (US); Stuart A. Tison, McKinney, TX (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 15/123,221

(22) PCT Filed: Mar. 17, 2015

(86) PCT No.: PCT/US2015/020902
§ 371 (c)(1),
(2) Date: Sep. 1, 2016

(87) PCT Pub. No.: WO2015/142805
PCT Pub. Date: Sep. 24, 2015

(65) Prior Publication Data
US 2017/0108427 A1   Apr. 20, 2017

Related U.S. Application Data (60) Provisional application No. 61/954,500, filed on Mar. 17, 2014.

(51) Int. Cl.
*G01N 21/03* (2006.01)
*G01N 21/41* (2006.01)

(52) U.S. Cl.
CPC ..... *G01N 21/0303* (2013.01); *G01N 21/4133* (2013.01); *G01N 2021/0321* (2013.01); *G01N 2021/0364* (2013.01); *G01N 2021/0389* (2013.01); *G01N 2021/414* (2013.01)

(58) Field of Classification Search
CPC ........... G01N 21/0303; G01N 21/4133; G01N 2021/0321; G01N 2021/0364; G01N 2021/0389; G01N 2021/414
See application file for complete search history.

(56) References Cited

U.S. PATENT DOCUMENTS

| | | | |
|---|---|---|---|
| 5,526,956 A | 6/1996 | Osgar | |
| 6,077,356 A * | 6/2000 | Bouchard | B01J 4/008 118/715 |
| 6,698,619 B2 | 3/2004 | Wertenberger | |

(Continued)

FOREIGN PATENT DOCUMENTS

WO   WO2012/078977 A2   6/2012

OTHER PUBLICATIONS

International Search Report and Written Opinion issued for PCT Application No. PCT/US2015/020902, dated May 27, 2015, 10 pages.

*Primary Examiner* — Sang Nguyen
(74) *Attorney, Agent, or Firm* — Entegris, Inc.

(57) ABSTRACT

Embodiments as disclosed herein may provide a sensor system including a container, such as a bag, having a port assembly integrated therewith. The port assembly includes an optically transparent window and be configured such that a sensor may be mechanically attached to the port assembly to interface with the optical window. The sensor may include an index of refraction (IoR) sensor that measures the chemical concentration of a liquid inside the container based on a refractive index.

9 Claims, 6 Drawing Sheets

(56) References Cited

U.S. PATENT DOCUMENTS

| | | | |
|---|---|---|---|
| 7,674,254 B2 | 3/2010 | Baumfalk | |
| 7,916,285 B2 | 3/2011 | Amamiya | |
| 8,708,319 B2* | 4/2014 | Terentiev | B01F 3/04248 |
| | | | 261/121.1 |
| 2006/0158653 A1* | 7/2006 | Chiarello | B82Y 15/00 |
| | | | 356/445 |
| 2006/0243755 A1* | 11/2006 | Hennen | B67D 7/0294 |
| | | | 222/464.1 |
| 2006/0283932 A1* | 12/2006 | Asp | B65C 7/00 |
| | | | 235/375 |
| 2007/0070330 A1* | 3/2007 | Chiarello | G01N 21/0303 |
| | | | 356/136 |
| 2007/0070331 A1* | 3/2007 | Chiarello | G01N 21/0303 |
| | | | 356/136 |
| 2009/0131737 A1* | 5/2009 | Ferren | A61B 1/00156 |
| | | | 600/12 |
| 2010/0296079 A1* | 11/2010 | Chiarello | G01N 21/43 |
| | | | 356/72 |
| 2012/0267388 A1 | 10/2012 | Tom | |
| 2013/0036799 A1* | 2/2013 | Silveri | G01N 27/4168 |
| | | | 73/61.41 |
| 2013/0214138 A1 | 8/2013 | Chiarello | |
| 2015/0125347 A1* | 5/2015 | Machuca | G01N 33/18 |
| | | | 422/82.07 |

\* cited by examiner

DISPOSABLE LIQUID CHEMICAL SENSOR SYSTEM

CROSS-REFERENCE TO RELATED APPLICATIONS

This is a national stem application of International Application No. PCT/US2015/020902, filed Mar. 17, 2015, entitled "DISPOSABLE LIQUID CHEMICAL SENSOR SYSTEM," and claims a benefit of priority to U.S. Provisional Patent Application Ser. No. 61/954,500 filed Mar. 17, 2014, entitled "DISPOSABLE LIQUID CHEMICAL CONCENTRATION AND TEMPERATURE SENSOR SYSTEM ", all of which are incorporated herein in their entirety by reference for all purposes.

TECHNICAL FIELD

This disclosure relates generally to sensor systems. In particular, this disclosure relates to sensor systems, including chemical concentration, temperature or other sensor systems, configured for use in single use systems.

BACKGROUND

Conventionally, chemical manufacturing applications are executed within reusable stainless steel systems. However, single-use (e.g., disposable) technology (SUT) and in particular, single-use systems (SUS) such as bags or the like are a fast growing technology innovation for the biotechnology and biopharmaceutical manufacturing markets. SUS are used in a wide variety of biopharmaceutical manufacturing applications (both upstream and downstream applications), particularly in clinical testing and research and development.

SUS offers several advantages over conventional reusable stainless steel systems by reducing contamination risk, reducing the amount of cleaning time and chemicals required for each process, and reducing the number and/or complexity of necessary system validation steps. Some additional benefits of employing SUS include flexibility, scalability, and speed of implementation.

Accordingly, SUS are presently deployed in systems ranging from bioreactors to mixing systems. Examples of upstream applications that currently use SUS include media preparation processes such as mixing, clarification, and sterilizing filtration. Examples of downstream applications that currently use SUS include cell harvesting, clarification, chromatography concentration and diafiltration, contaminant removal, and buffer preparation.

The control of such processes requires accurate measurements of a number of process parameters, including, for example, the temperature or concentration of the chemicals involved in the process. As such, with the growing use of SUS it is desired to measure these process parameters in conjunction with these SUS. Doing so, however, has not proved straightforward or effective. In no small part efforts to do so have been frustrated by the fact that sensors must be integrated with the SUS. It is difficult to interface a sensor with containers used in SUS, such as a bag, and still obtain accurate measurements. In no small part this may be because certain sensors may need to contact the chemical itself to obtain an accurate measurement or may measure parameters indirectly (e.g., measure a proxy for a parameter). Additionally, the cost of such sensors is problematic. When an instance of a process is completed, the SUS may be disposed of, including the sensor. As the sensors may be expensive, the constant disposal of such sensors may increase the costs of manufacturing the chemicals using such SUS.

What is desired then, are systems and methods to effectively integrate sensors into SUS to improve data collection for use in process control or management. It is especially desired to provide effective and relatively low cost systems and method for effective chemical concentration or temperature measurement in these SUS.

SUMMARY

To that end, embodiments as disclosed herein may include, a disposable sensor in a miniaturized single fully integrated interface package configured to be interfaced with a single use system. Embodiments of such a sensor may include, for example, a chemical concentration or temperature sensor. The sensor may be interfaced with an electronic control and data communications module which may be configured to interface multiple sensors.

Each disposable sensor is readily interfaced to a disposable container such as a polymeric bag, liner, overpack or the like. Such an interface may be accomplished using a sterile method. In some embodiments, the container may be interfaced using a port assembly integrated with the container. The port assembly includes an optically transparent window and be configured such that the sensor may be mechanically attached to the port assembly to interface with the optical window using, for example, a threaded attachment or a snap in connector. This window may, for example, be borosilicate glass, sapphire or another optically transparent material.

In embodiments, the sensor includes an index of refraction (IoR) sensor that measures the chemical concentration based on a refractive index. This optical measurement may be a true concentration measurement, offering advantages over measurements of pH and conductivity that are provided by conventional SUS standalone sensors.

To avoid air between the optical sensor and the optically transparent window (which may distort such an optical measurement), an optically transparent or IoR matching fluid may be disposed between the sensor and the window of the flange. Such a fluid may, for example, be placed on the window before the sensor is attached to the flange.

Accordingly, in addition to other advantages, embodiments may provide the advantages that result from coupling an optical sensor, such as an Index of Refraction (IoR) concentration sensor, to a SUS including bags or the like. These advantages may include sensitivity, accuracy or other functional advantages. For example, certain connectivity sensors will not work in non-ionic species, while IoR sensors may function in conjunction with such species and without being in physical contact with a sample itself. Embodiments may thus provide a true concentration sensor that may be utilized with a wide variety of chemicals, including non-ionic species. Moreover, such sensors may be relatively fast in producing a measurement compared to other sensors, such as those that require grab samples or the like.

Additionally, by providing a port assembly in the container where the sensor may be later mechanically attached to the port assembly a wide variety of sterilization procedures may be utilized with such a bag, without concern for the sensor, including irradiation or the like. Because of this advantage the single use sensors used in conjunction with such sensor system may not need to be designed to withstand such sterilization procedures which may, in turn, reduce the cost of such sensors and the corresponding systems that include the single use sensor systems.

Moreover, embodiments where a concentration and a temperature sensor are integrated into a single platform may offer several advantages compared to conventional SUS sensor systems. The integration eliminates the need for the multiple bag ports that each would be required for a respective standalone sensor. A single electronic controller module configured to connect to multiple sensors reduces SUS configuration costs and enables improved data collection and management for monitoring and control systems.

These, and other, aspects and advantages of the disclosure will be better appreciated and understood when considered in conjunction with the following description and the accompanying drawings. The following description, while indicating various embodiments and numerous specific details thereof, is given by way of illustration and not of limitation. Many substitutions, modifications, additions or rearrangements may be made within the scope of the disclosure, and the disclosure includes all such substitutions, modifications, additions or rearrangements.

BRIEF DESCRIPTION OF THE DRAWINGS

Having thus described the invention in general terms, reference will now be made to the accompanying drawings, which are not necessarily drawn to scale. A more complete understanding of the embodiments and the advantages thereof may be acquired by referring to the following description, taken in conjunction with the accompanying drawings in which like reference numbers indicate like features and wherein:

DETAILED DESCRIPTION

The disclosure and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure.

As discussed above single-use systems (SUS) offers several advantages over conventional reusable stainless steel (or other) systems and are presently deployed in a variety of systems ranging from bioreactors to mixing systems. Before discussing particular embodiments in more detail it may first be helpful to give some brief background information. In chemical applications, including manufacturing applications, in the context of life sciences or biopharmaceuticals a quick turnaround time is often required. However, many reusable manufacturing devices (e.g., bioreactors or the like) may take a long time to clean, sterilize or otherwise prepare for the manufacturing of another batch of chemicals. Hence, many of these manufacturing processes have started to utilize SUS. Specifically, a single use container is used for a process then discarded. SUS offers several advantages over conventional reusable stainless steel systems by reducing contamination risk, reducing the amount of cleaning time and chemicals required for each process, and reducing the number or complexity of necessary system validation steps.

Accordingly, SUS are presently deployed in systems ranging from bioreactors to mixing systems, among others. However, the processes with which these SUS are utilized are, in many cases, highly sensitive to certain process parameters. Accordingly, to adequately manage or otherwise control these processes it is important to be able to accurately measure such process parameters. The integration of sensors with the single use containers used in SUS in order to measure these parameters has, however, not heretofore been successful. It is not only difficult to interface a sensor with these single use containers (e.g., a bag, liner, overpack, etc.) and still obtain accurate measurements but, additionally, the cost of such sensors is problematic.

Figure 1:
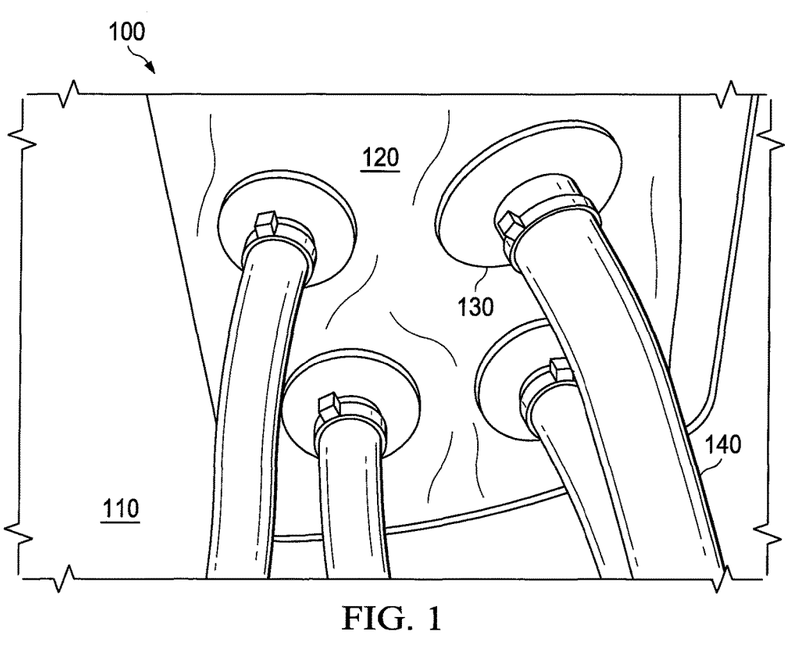
FIG. 1 illustrates one embodiment of a single use system using a disposable bag configured for a chemical mixing process.

Processes, storage or transportation of chemicals may involve the use of a container. Turning now to FIG. 1 a diagram of a typical SUS configuration 100 for chemical mixing, or other type of process, is depicted. Mixing process may execute within a container such as a polymeric bag, liner or overpack. Such a container may be utilized in a standalone configuration or may be installed into a vessel such as reusable stainless steel (or other type of) vessel 110. The container may thus be part of a bag in a bottle (BIB) or bag in a container (BIC) system. The container, such as disposable polymeric bag 120, will be discarded after use (e.g., a chemical mixing process, transport of chemicals using the container, etc.) concludes.

As these types of containers may be used in wide variety of processes that may require the use of sterile or non-sterile containers; may be used in a wide variety of industries (e.g., life sciences, pharmaceutical, semiconductor fabrication, etc.) and with a wide variety of caustic or non-caustic chemicals (e.g., hydrogen fluoride, hydrogen sulfide, hydrogen peroxide and ammonium hydroxide, acids, solvents, bases, photoresists, slurries, cleaning formulations, dopants, inorganic, organic, metalorganic, biological solutions, pharmaceuticals, radioactive chemicals, silicon source compounds, chemical mechanical planarization (CMP) compositions, etc.), these types of containers made by made out of a wide variety of materials. These materials may include for example, polymers, including plastics, nylons, EVOH, polyolefins, or other natural or synthetic polymers, polyethylene terephthalate (PET), polyethylene naphthalate (PEN), poly (butylene 2,6-naphthalate) (PBN), polyethylene (PE), linear low-density polyethylene (LLDPE), low-density polyethylene (LDPE), medium-density polyethylene (MDPE), high-density polyethylene (HDPE), and/or polypropylene (PP). a fluoropolymer, such as but not limited to, polychlorotrifluoroethylene (PCTFE), polytetrafluoroethylene (PTFE), fluorinated ethylene propylene (FEP), perfluoroalkoxy (PFA), ethylene tetrafluoroethylene (ETFE) including those sold by Dupont under the trademark Tefzel® etc.

In the embodiment illustrated, chemicals used in the process enter the bag 120 through chemical delivery tubing 140 attached to a bag port. Each chemical delivery tube 140 has a mechanical attachment to each bag port at a flange 130 on the external surface of the bag. Conventionally, standalone sensors for use with such a bag 120 measure chemical attributes such as pH, conductivity, or temperature. Each of these standalone sensors is installed into a port. Using multiple standalone sensors thus requires a container, such as bag 120, to be configured with multiple ports. Bag ports are sources of additional cost and contamination, and they usually require tech support for implementation (e.g., calibrations) and attachment.

It is thus desired to provide cost effective solutions to improve measurement of chemical parameters, including chemical concentration or temperature, in SUS. To that end, embodiments as disclosed herein may include a container such as a bag having a port assembly integrated therewith, where the port assembly includes an optically transparent window. This window may, for example, be borosilicate glass, sapphire or another optically transparent material. A sensor may be mechanically attached to the port assembly (e.g., whereby the sensor can interface with the optical window) using, for example, a threaded connection, a snap in connection, adhesive, etc.).

Embodiments of such a sensor may include, for example, a chemical concentration (including, for example, analyte concentration) or temperature sensor. The sensor may be interfaced with an electronic control and data communications module which may be configured to interface with one or more sensors. This interface may, for example, be accomplished by coupling the control module to the sensor using a Turk or a Hiroshi connector that is configured to mechanically or communicatively be coupled to the sensor. Such a sensor, may, for example, be an optical concentration sensor for measuring chemical concentration utilizing an optical measurement based on refractive index principles. Embodiments of such a sensor may also measure the temperature, or other properties, of the chemical.

Figure 2:
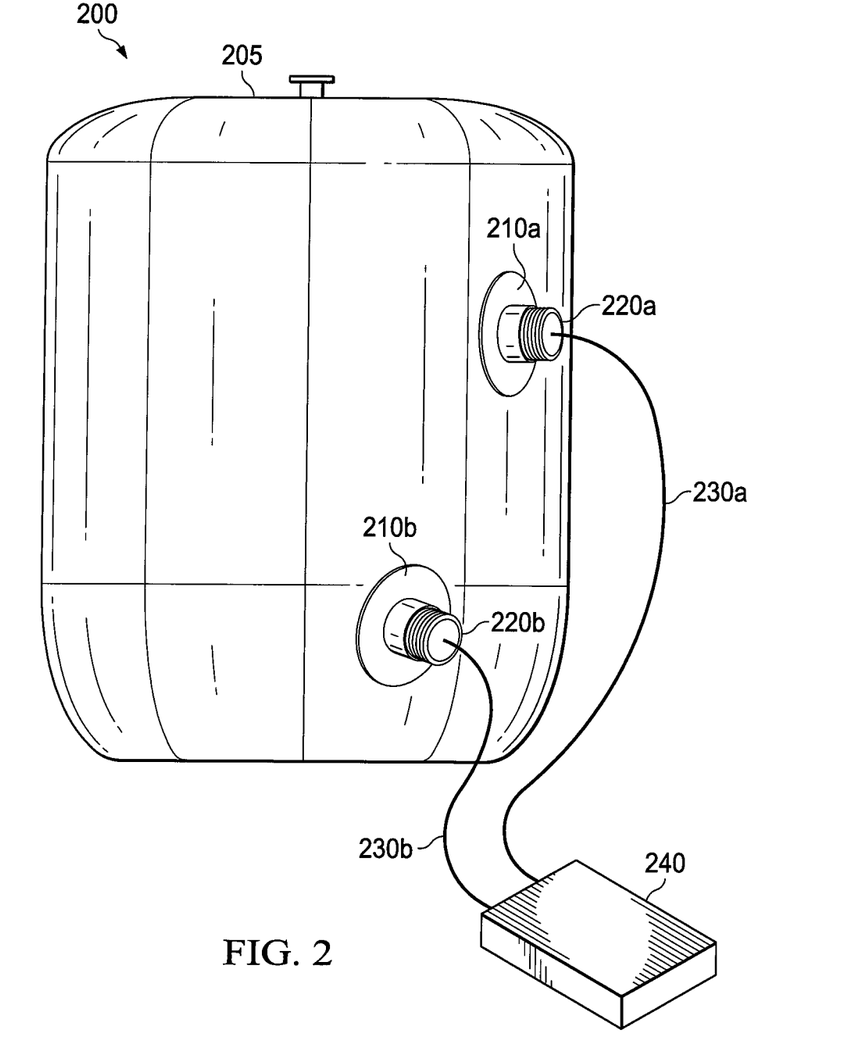
FIG. 2 is a diagram of one embodiment of a single use system that is configured to include a disposable sensor system.

FIG. 2 is a diagram of one embodiment of a SUS 200 that includes a container 205 such as a bag, liner, overpack or the like that is configured to include a disposable sensor system, including for example, a disposable liquid chemical concentration and temperature sensor system. The disposable liquid chemical concentration and temperature sensor system comprises an electronic control and data communications module 240 that is configured to connect respectively to one or more disposable sensors via a cable (230a and 230b).

In embodiments, one or more of the sensors is an optical sensor that is configured to interface with an optical window in the disposable container 205. In such cases, a port assembly may include flange 210 and may be integrated with the bag, where an optically transparent window is disposed in the flange so that the window is in contact with fluid in the container 205 (when fluid is present in container 205). This window may, for example, be borosilicate glass, sapphire or another optically transparent material such as an optically transparent polymeric material such as ethylene tetrafluoroethylene (ETFE). Each optical sensor is respectively affixed to the external surface of the disposable container 205 at the optical window of the flange 210 in the bag using a mechanical mechanism. The optical sensor may, for example, be potted into sensor assembly including a receptacle 220 (e.g., 220a or 220b) and the receptacle 220 may be mechanically coupled to the flange 210 using, for example, a threaded or snap in connector, such that the sensor can interface with the optical window of the flange 210.

In certain cases, a connector (not shown) may be mechanically or communicatively coupled to the sensor potted into receptacle 220 and provide a connector (e.g., a Turk or a Hiroshi connector) through which electronic control and data communications module 240 may be coupled (e.g., mechanically or communicatively) to the sensor. Such a connector may be, for example, a bonnet that is configured to mechanically attach (e.g., by threads or snap in connector) to the leads, or another electronic interface, of the sensor and provide one or more signals of the sensor through the connector to which the electronic control and data communications module 240 is coupled.

Figure 3A:
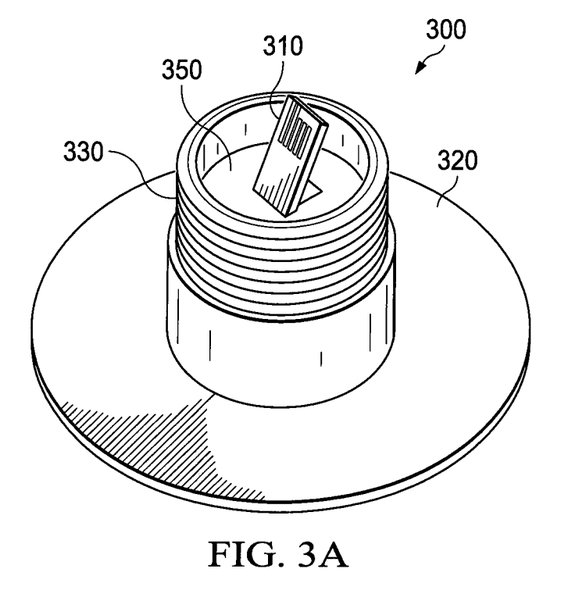
FIG. 3A depicts a top view of an one embodiment of an interface of a disposable sensor to a disposable container.
Figure 3B:
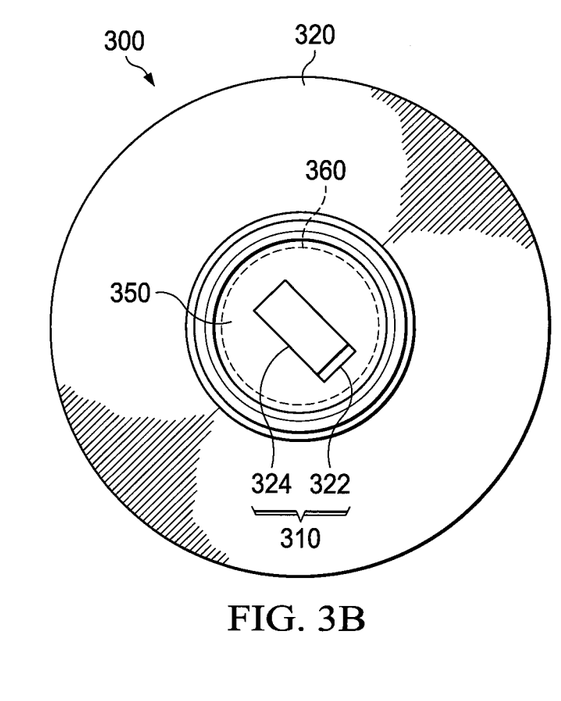
FIG. 3B depicts a bottom view of one embodiment of interface of a disposable sensor to a disposable container.

FIGS. 3A and 3B each depict views of one embodiment of a port fitting configured to be integrated into a disposable container such as a bag to interface a sensor with the disposable container. Specifically, FIG. 3A depicts a top view of one embodiment while FIG. 3B depicts a bottom view of the embodiment, Here, port assembly 300 is configured to be mechanically integrated with a disposable bag such that an optical window of the port assembly 300 is exposed to the inside of the disposable bag and a disposable optical sensor is interfaced with the optical window. Port assembly 300 may be made of a material stable to gamma radiation, including such gamma stable polymeric materials including, for example, polyvinyl chloride, polyvinyl fluoride or polyvinyl acetate, or other polymers such as fluorinated ethylene propylene (FEP), ethylene tetrafluoroethylene (ETFE), polyethylenes like high density polyethylene or low density polyethylene, polyvinylidene fluoride, ethylene tetrafluoroethylene, polyimides, etc.

More specifically, top view of port assembly 300 depicts the portion of the port fitting 300 that would face the external surface of a disposable bag with which it is integrated. This view illustrates the mechanical attachment of the sensor 310 to the external surface of the disposable bag. In embodiments, the disposable optical sensor 310 is potted into a cap 330 (which may also be made of a gamma stable polymeric material as discussed above) using a potting material composed of, for example, either alumina or a silicon-based material (e.g., Room Temperature Vulcanizing (RTV) silicone). In embodiments in which the optical sensor 310 is potted into cap 330, the thermal conductivity of the potting material may facilitate temperature measurement by thermal sensor 324. The cap 330 is then welded, using an optical epoxy, into a disposable optical connector flange 320 that is located at optical window 350 integrated with disposable bag and where the inner surface of the optical window 350 is exposed to the inside of the disposable bag. One example of a sensor 310 is an SRSENSOR by Entegris-Jetalon Solutions, Inc. of Pleasant Hill, Calif. Other embodiments of such a sensor are disclosed in U.S. patent application Ser. No. 13/401,765, U.S. Pat. Nos. 7,319,523, and 7,317,533, which are hereby incorporated by reference in their entirety.

FIG. 3B depicts a bottom view of port assembly 300 looking towards sensor 310 (within the cap 330 that is welded into the optical connector flange 320). This portion of port assembly 300 exposes the optical window to the inside of the disposable bag and this view illustrates the interface between the sensor 310, the optical window and the disposable bag. Optical sensor 310 may include a liquid concentration sensor 322 and thermal sensor 324.

In embodiments, the optical sensor 310 is bonded to an optically transparent window 360 (such as borosilicate glass or sapphire) that interfaces with the optical window 350 which inner surface is exposed to the inside of the disposable bag. In embodiments, the optical window 350 is composed of an optically transparent material (e.g., borosilicate glass, sapphire, diamond, or ah optically transparent polymeric material such as fluorinated ethylene propylene (FEP), ethylene tetrafluoroethylene (ETFE)) that is chemically inert. The interface between the sensor glass window 360 and the optical window 350 is filled with an index of refraction (IoR)-matching material (e.g., oil, gel, or epoxy) to ensure that the surfaces bond without an air gap between them. The IOR-matching material that is used in a particular interface may be selected to match the IoR of the optical window in the disposable bag.

It will be noted that while this embodiment depicts the optical sensor 310 bonded to an optically transparent window 360 that interfaces with the optical window 350 exposed to the inside of the disposable bag, in other embodiments the optically transparent window 360 may be eliminated. In such embodiments, optical sensor 310 may directly contact optical window 350, or may be separated a working distance from optical window 350, where there may be an IoR-matching material disposed between the optical sensor 310 and the optical window 350.

Figure 4:
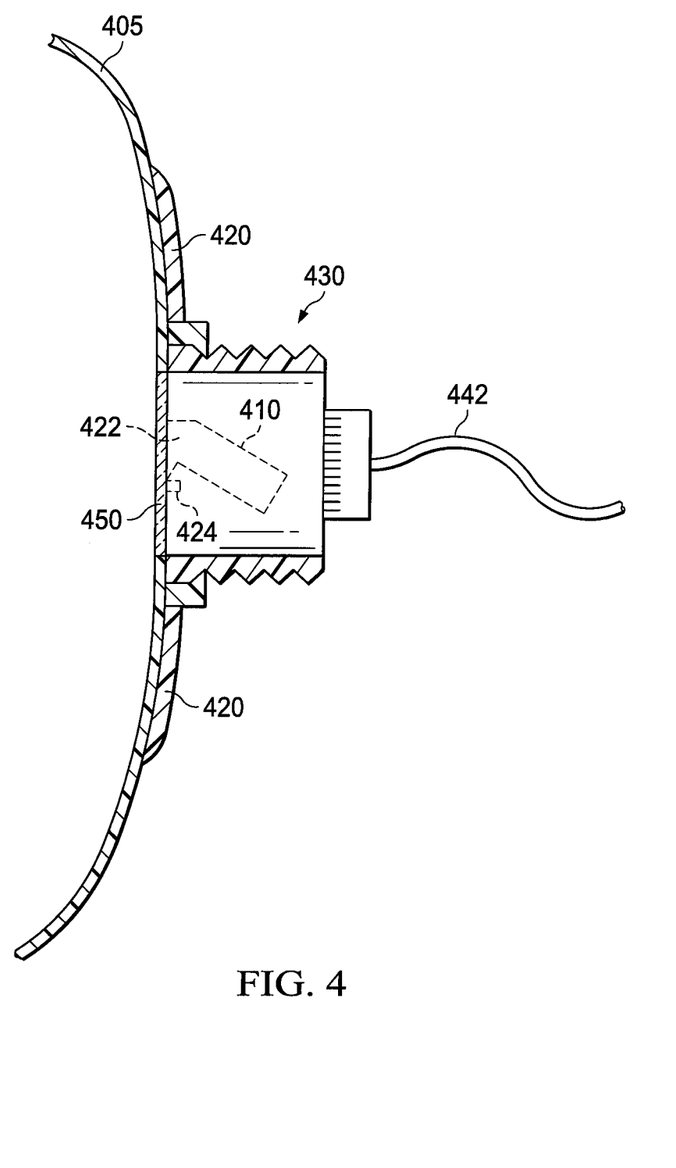
FIG. 4 depicts a cross section of one embodiment of interface of a disposable sensor to a disposable container.

FIG. 4 is a diagram of a disposable optical sensor 410 that is interfaced to an optical window 450 in a disposable bag 405 according to various embodiments of the invention. The optical sensor 410 is potted into a receptacle 430 that is attached to the external surface of a disposable bag 405 at an optical window 450 via an optical connector flange 420, as previously described. Optical sensor 410 includes a liquid chemical concentration sensor 422 and a thermal sensor 424 adjacent to optical window 450.

In embodiments, the optical sensor 410 is communicatively coupled via a cable 442 to an electronic control and data communications module. As described previously with respect to FIG. 2, a SUS can be configured to include multiple optical sensors, and a single electronic controller module can be configured to connect simultaneously to all of the optical sensors.

Figure 5A:
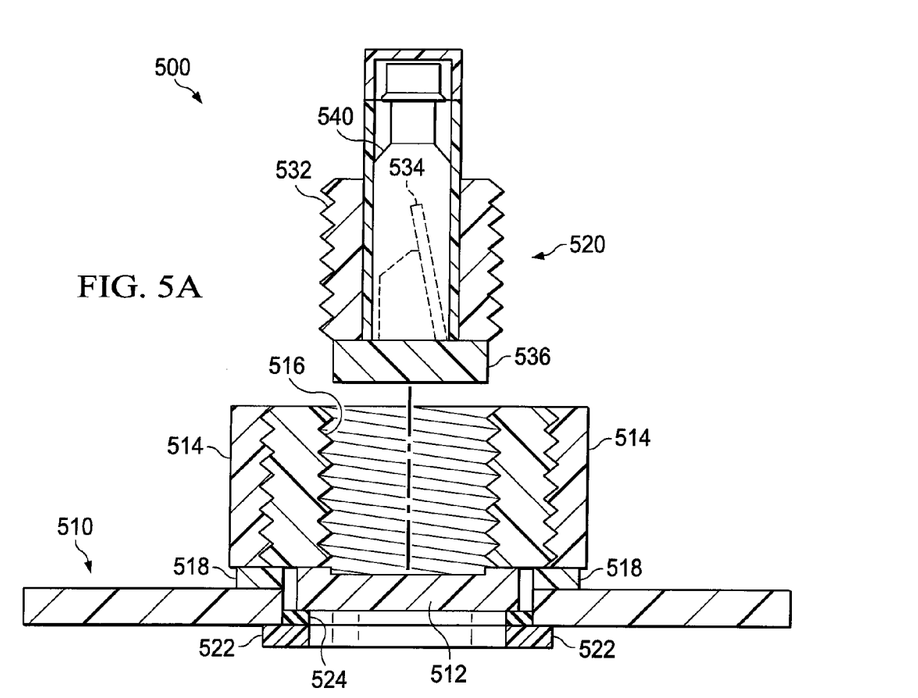
FIGS. 5A and 5B are a diagram of a disposable optical sensor that is interfaced to an optical window in a disposable container.
Figure 5B:
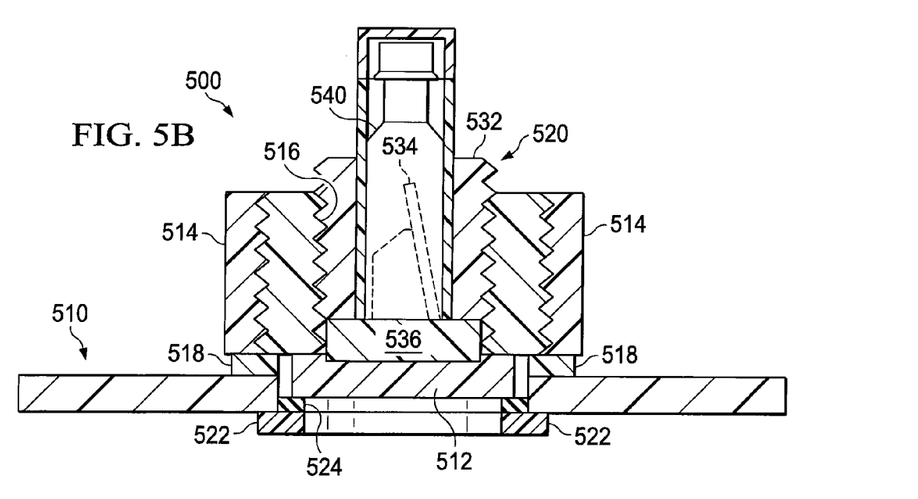

Another embodiment of disposable optical sensor system is depicted in FIGS. 5A and 5B. The optical sensor system 500 includes a port assembly 510 and sensor assembly 520. FIG. 5A depicts the port assembly 510 and sensor assembly 520 in a decoupled state while FIG. 5B depicts the port assembly 510 and sensor assembly 520 in a mechanically coupled state. The materials of the port assembly 510 (and in some cases the sensor assembly 520) can include materials selected to be gamma stable (such as those discussed above) or withstand other sterilization procedures such as E-beam, ozonated water, etc.

The port assembly 510 can also include a port window 512 that can be integrated with the bag using a mounting technique that will seal the window 512 with the bag such as injection molding (including overmolding or the like) or using a threaded style insertion and compression seal. In this manner, an inner surface of the window 512 will be exposed to the inside of the bag and the outer surface, opposite the inner surface, will be exposed on the outer surface of the bag.

In the embodiment depicted, port assembly 510 may include an annular outer nipple 514 threaded on the inner diameter and an annular inner nipple 516 threaded on the inner diameter and the outer diameter. Port assembly 510 may also include annular outer ring 518 (which may be formed as part of the outer nipple 514) and annular inner ring 522, Window 512 may be disposed on annular inner ring 522 or, in some embodiments, annular o-ring sea 524 may be disposed between the window 512 and the annular inner ring 522. When inner nipple 516 is threaded into the inner threads of annular outer nipple 514 it may contact at least window 512 (and in some embodiments may also contact at least a portion of annular outer ring 518). Inner nipple can be tightened with sufficient force that a fluid tight seal may be formed between window 512 and annular inner ring 522 (or between inner ring 522, window 512 and o-ring). Thus, the sensor assembly 520 may be mechanically affixed to a bag with window 512 that is in contact with any fluid that may be in the bag and where a portion of the window 512 is exposed through the opening in inner nipple 516.

Port assembly 510 may thus be integrated with a single use bag, tubing or other component of a system. The bag, tubing or other component can be sterile. In some cases, such a port assembly 510 may be part of a flow through device, such as a tube or other component. The component may use aseptic (sterile) input and/or output connectors to connect to other portions of the system. Thus, for example, a flow through device providing a sensor port can be connected/disconnected in a sterile environment.

In some cases, the port assembly 510 may be coupled to, or otherwise integrated with, a component of a system through which liquid flows, such as tubing outside of a bag. By way of example, but not limitation, a recirculation loop could be provided for a single use bag in which a pump (such as a peristaltic pump or other pump) pumps fluid from the single use bag, through a loop back to the bag. The port assembly 510 can be integrated in a wall of the loop so that fluid flows past the port window.

Moving now to sensor assembly 520, the sensor assembly 520 can include a threaded cap 532 with a sensor 534 bonded thereto. Threaded cap 532 may be cylindrical and have threads on its outer diameter. For example, the sensor 534 may be potted into the threaded cap 532. Optionally, the sensor assembly 520 may also include a sensor window 536 and the sensor 534 may be bonded to the sensor window 536 using an adhesive or the like.

Sensor assembly 520 can be threaded into inner nipple 516 such that the threads on the outer surface on the threaded cap 532 engage the threads on the inner surface of the inner nipple 516. The threaded cap 532 can then be tightened until the sensor 534 (or, in certain embodiments sensor window 536) contacts, or is a desired working distance, from window 512. In this manner, the sensor 534 may be interface with the outer surface of the port optical window 512. It will be understood that while embodiments have been described as using threaded nipples to mechanically attach the sensor to the port, in other embodiments the port assembly can receive the sensor using other mechanisms. For example, using retaining clips, etc.

When the sensor assembly 520 is in place the sensor optical window 536 and port optical window 512 can contact (or be a working distance from one another), or the surface of the sensor 534 may contact (or be a working distance from) the port optical window 512 if the sensor assembly 520 does not include sensor window 536. In such cases the surfaces (e.g., the surfaces of the port window 512 and sensor window 536 or the surface of port window 512 and the surface of the sensor 534 contacting the port window 512) may bond. In one embodiment the surfaces may bond through van der Waals forces or in other embodiments, an intermediary material can be used, such as silicone oil, optical epoxy or other material. The intermediary material may be an IoR matching material which may, for example, match the IoR of the port window or the sensor window. Additionally, to encourage such bonding, the surfaces may be polished.

A snap on connector may then be attached to the sensor to couple the sensor 532 to a control module or other device. In one embodiment, bonnet 540 may include a snap on connector configured to be mechanically and communicatively coupled to the sensor. Bonnet 540 may also include a connector (e.g., a Turk or a Hiroshi connector) to which a cable may be connected to provide signals from the senor to an electronic control or data communications module. In some embodiments, an intermediate microprocessor is included in the bonnet 540 for signal amplification or other processing.

In embodiments, the optical sensor (e.g., optical sensor 310, 410 or 534) is a refractive index sensor that measures liquid chemical concentration based on refractive index principles. Conventionally, refractive index is measured using bulky and expensive laboratory instruments (e.g., bench to refractometers or complex in-line chemical monitoring equipment). The refractive index of the liquid chemicals inside of the bag may be computed at the disposable sensor using at least one disposable miniaturized optical path that includes a light source, a prism, a reflecting window, and a detector for optically reflected light.

Use of a refractive index sensor in a SUS provides several advantages over sensors that are conventionally used in SUS. Refractive index measures the total concentration of all components in a liquid, while pH and conductivity sensors (the standalone sensors that typically are used in a SUS) are limited to only the H+ and ionic components of the liquid, respectively. Refractive index is linearly related to concentration and is easily calibrated. A refractive index sensor can thus measure concentrations of fluids or chemicals regardless of whether they are clear or opaque. A refractive index sensor can be used as a chemical compound speciation device by using the wavelength dispersion of the refractive index. Determining speciation typically is performed using costly absorption spectroscopy techniques (e.g., near-infrared absorption spectroscopy) that are incompatible with systems based on SUS. A refractive index sensor is also readily interfaced to an optical window in a disposable bag using a sterile method, as previously described.

In embodiments, a refractive index sensor as utilized with a SUS may be manufactured using miniature components that include a miniature printed circuit board (PCB hereinafter) for holding die mounted LEDs, LED control circuitry, and the receiving electronics for the optically reflected light. The receiving electronics for the optically reflected light are used to scale, amplify, and read out analog or digital signals that are transmitted from the sensor, and, in embodiments, may include a photodiode array and/or a charge-coupled device with circuit drivers.

The optical sensor may also include non-volatile memory to store, for example, data collected from an executing chemical process and processed in real-time. Examples of types of data collected include calibration tables, the sensor identifier, temperature compensation coefficients, and pressure/flow rate compensation coefficients.

In embodiments, the optical sensor further includes a thermal sensor. As is known in the art, the index of refraction has a functional dependence on temperature as well as on chemical concentration. Although the index of refraction is theoretically referenced to an operation occurring at a constant temperature (e.g., 20 degrees Celsius), a sensor taking measurements during a chemical process typically is exposed to fluctuating temperatures. When the index of refraction is used for concentration monitoring in real-time, each shift in temperature also can be detected as a change in concentration.

To detect temperature variations that are occurring during an executing chemical process, a first thermal sensor may be located on the optical sensor window of certain embodiments and a second thermal sensor integrated into a printed circuit board of the optical sensor. Data representing detected temperature variations may be collected and stored within the non-volatile memory of the optical sensor.

Temperature data that is collected by thermal sensors may be input to various methods, implemented as software and/or firmware that can be executed by the optical sensor (or otherwise) to make real-time temperature compensation during an executing chemical process. For example, in embodiments, a first method may calculate a correlation coefficient that is dependent on a chemical under test and the thermal environment within the SUS, the calculation being based on comparing collected data representing the slow variation in temperature to collected data representing the variation in chemical concentration. Additionally or alternatively, a second method may calculate a temperature fluctuation rate correction term derived from the correlation between the varying chemical concentrations with respect to the derivative of the temperature. This rate correction term may be used to correct for fast transient changes in temperature. These fast transient changes in temperature may be characteristic of scenarios such as adding a new chemical into existing bio-reactors, or which may result from non-equilibrated flowing chemical over small sensors that do not have enough thermal mass to dampen temperature changes. The slow varying temperature correction can be applied in conjunction with the fast transient correction to enable overall temperature compensation during an executing chemical process (e.g., chemical injection cycle, a reaction cycle, etc.).

Figure 6:
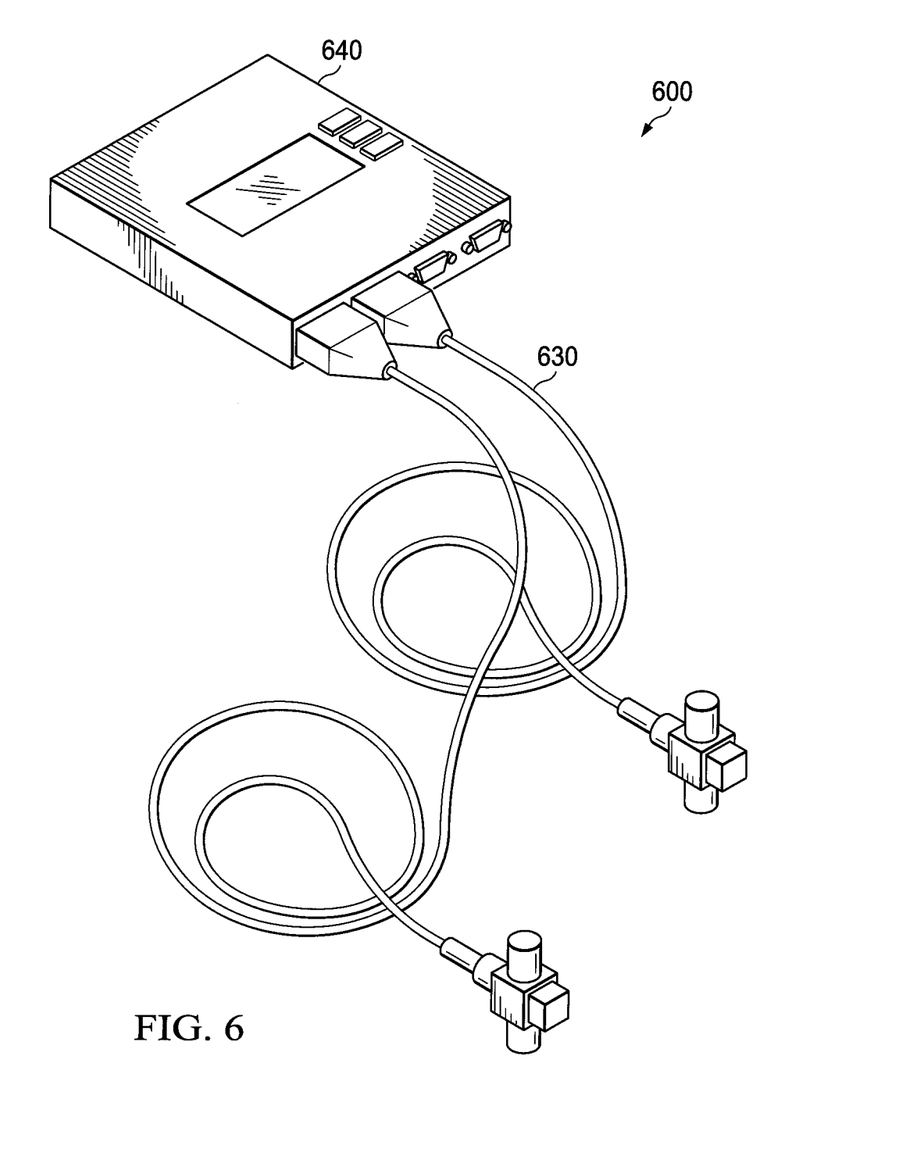
FIG. 6 is one embodiment of an electronic controller module configured to connect to two disposable optical sensors in accordance with some embodiments discussed herein.

FIG. 6 is a diagram of an exemplary electronic controller module 600 configured to connect to two disposable optical sensors according to various embodiments of the invention. The exemplary electronic controller module 640 is a Jetalon CR-288 all-purpose liquid chemical concentration monitor. Each of the two cables 630 respectively ends in a flow cell that includes a sensor head. In some embodiments, the two cables 630 may be terminated in connectors that are configured to mate with a connector (e.g., a Turk or a Hiroshi connector) coupled to the optical sensor as described.

As used herein, the terms comprises, comprising, includes, including, has, having or any other variation thereof, are intended to cover a non-exclusive inclusion. For example, a process, product, article, or apparatus that comprises a list of elements is not necessarily limited to only those elements but may include other elements not expressly listed or inherent to such process, article, or apparatus. Further, unless expressly stated to the contrary, or refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. For example, as discussed above, while embodiments depicted herein have been illustrated utilizing a polymeric bag, it will be noted that embodiments as depicted herein may be equally effectively utilized with liners (e.g., polymeric liners) or overpacks utilized, for example, in liner based applications such as for storage or dispensing systems (e.g., BIB or BIC systems). Such liners include for example, tubular or cylindrically shaped liners having welded bodies, collapsible or flexible liners, rigid liners, extruded liners, liners with or without gussets, standalone liners, liners utilized in a receptacle or vessel, etc. Such bags, liners and overpacks are illustrated in U.S. Pat. No. 5,526,956, titled "Liquid Chemical Dispensing and Recirculating System," filed on Jul. 1, 1994; U.S. Pat. No. 6,698,619, titled "Returnable and Reusable, Bag-in-Drum Fluid Storage and Dispensing Container System," filed on May 3, 200;, United States Patent Application Publication No. 2012/0267388, titled "Substantially Rigid Collapsible Liner and Flexible Gusseted or Non-Gusseted Liners and Methods of Manufacturing the Same and Methods for Limiting Choke-Offs in Liners," published Oct. 25, 2012 and International PCT Appl. No. PCT/US2011/064141, titled "Generally Cylindrically-Shaped Liner for Use in Pressure Dispense Systems and Methods of Manufacturing the Same," filed on Dec. 9, 2011; International PCT Appl. No. PCT/US2012/070866, titled "Liner-based Shipping and Dispensing Systems," filed Dec. 20, 2012; International PCT Appl. No. PCT/US11/55558, titled, "Substantially Rigid Collapsible Liner, Container and/or Liner for Replacing Glass Bottles, and Enhanced Flexible Liners," filed Oct. 10, 2011; International PCT Appl. No. PCT/US11/55560, titled, "Nested Blow Molded Liner and Overpack and Methods of Making Same," filed Oct. 10, 2011; International PCT Appl. No. PCT/US11/64141, titled "Generally Cylindrically-Shaped Liner for Use in Pressure Dispense Systems and Methods of Manufacturing the Same," filed Dec. 9, 2011; U.S. Prov. Appl. No. 61/468,832, titled "Liner-Based Dispenser," filed. Mar. 29, 2011; U.S. Prov. Appl. No. 61/525,540, titled "Liner-Based Dispensing Systems," filed Aug. 19, 2011; U.S. patent application Ser. No. 11/915,996, titled "Fluid Storage and Dispensing Systems and Processes," filed Jun. 5, 2006; International PCT Appl. No. PCT/US10/51786, titled "Material Storage and Dispensing System and Method With Degassing Assembly," filed Oct. 7, 2010, International PCT Appl. No. PCT/US10/41629, U.S. Pat. No. 7,335,721, U.S. patent application Ser. No. 11/912,629, U.S. patent application Ser. No. 12/302, 287, and International PCT Appl. No. PCT/US08/85264, each of which is hereby incorporated by reference herein in its entirety for all purposes.

Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: for example, for instance, e.g., in one embodiment, and the like.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as the presently preferred embodiments. Elements and materials may be substituted for those illustrated and described herein, parts and processes may be reversed, and certain features of the disclosure may be utilized independently, all as would be apparent to one skilled in the art after having the benefit of this description of the disclosure. Changes may be made in the elements described herein without departing from the spirit and scope of the disclosure as described in the following claims.

What is claimed is:

1. A disposable sensor system comprising: at least one disposable sensor assembly comprising a threaded cap with an index of refraction sensor bonded to the threaded cap, said index of refraction sensor measures a chemical concentration based on a refractive index, said sensor configured to perform data acquisition representing a chemical concentration, the disposable sensor assembly is affixed through a port assembly to a disposable polymeric bag container, the disposable polymeric bag comprising an optical window integrated with the disposable polymeric bag, the sensor assembly coupled to the disposable polymeric bag at an external surface of the optical window; an inner surface of the optical window is exposed to the inside of the polymeric bag container; said port assembly has an annular outer nipple threaded on the inner diameter and an annular inner nipple threaded on an inner diameter and an outer diameter, said port assembly has an annular inner ring, and the optical window is disposed on said annular inner ring whereby when inner nipple is threaded into the inner threads of annular outer nipple, inner nipple contacts at least said optical window; the sensor assembly threads into inner nipple whereby the threads on the outer threaded cap engage the threads on the inner surface of the nipple;

a first thermal sensor on the optical window and a second thermal sensor on the circuit board of the index of refraction sensor; and the sensor configured to be coupled to a control and data communications system configured to receive the data representing the chemical concentration from the at least one disposable sensor.

2. The disposable sensor system of claim 1, wherein the optical window is borosilicate glass, sapphire, diamond or an optically transparent polymer.

3. The disposable sensor system of claim 1, wherein the port assembly is comprised of a material that is stable to gamma radiation.

4. The disposable sensor system of claim 1, wherein the sensor assembly is a cap and the sensor is potted in the sensor assembly, wherein the cap is made of a polymeric material sterilized by gamma radiation .

5. The disposable sensor system of claim 1, wherein an index of refraction (IoR) matching material is disposed between the external surface of the optical window and the sensor.

6. The disposable sensor system of claim 5, wherein the IoR matching material matches the IoR of the optical window.

7. The disposable sensor system of claim 1, wherein the sensor assembly includes a sensor window and the sensor is bonded to the sensor window.

8. The disposable sensor system of claim 7, wherein an index of refraction (IoR) matching material is disposed between the external surface of the optical window and the sensor window.

9. The disposable sensor system of claim 1 , further including a connector configured to be mechanically coupled to the sensor and communicatively couple the sensor to the control and data communications system.

* * * * *